(12) United States Patent
Barak

(10) Patent No.: US 7,384,408 B2
(45) Date of Patent: *Jun. 10, 2008

(54) FLOW SET INCLUDING AN IDENTIFYING KEY MEMBER HAVING TWO PROJECTIONS COOPERATING TO DEFINE A UNIQUE CODE

(75) Inventor: Swi Barak, Caesarea (IL)

(73) Assignee: Caesarea Medical Electronics Ltd., Caesarea (IL)

( * ) Notice: Subject to any disclaimer, the term of this patent is extended or adjusted under 35 U.S.C. 154(b) by 166 days.

This patent is subject to a terminal disclaimer.

(21) Appl. No.: 10/113,866

(22) Filed: Apr. 1, 2002

(65) Prior Publication Data

US 2002/0177821 A1    Nov. 28, 2002

(30) Foreign Application Priority Data

Apr. 4, 2001   (IL)   ...................................... 142446

(51) Int. Cl.
*A61M 1/00*   (2006.01)
(52) U.S. Cl. ........................................ 604/30; 604/151
(58) Field of Classification Search ................ 604/513, 604/93.01, 80, 81, 131, 122, 158, 171, 181, 604/183, 186, 523, 30–34, 132, 151–153, 604/250–254, 246
See application file for complete search history.

(56) References Cited

U.S. PATENT DOCUMENTS

| 3,966,358 | A | | 6/1976 | Heimes et al. |
| 4,150,673 | A | * | 4/1979 | Watt ............................ 604/408 |
| 4,255,088 | A | | 3/1981 | Newton et al. |
| 4,277,226 | A | | 7/1981 | Archibald |
| 4,396,385 | A | | 8/1983 | Kelly et al. |
| 4,457,751 | A | | 7/1984 | Rodler |
| 4,460,535 | A | | 7/1984 | Kitoh et al. |
| 4,617,014 | A | | 10/1986 | Cannon et al. |
| 4,690,673 | A | * | 9/1987 | Bloomquist .................. 604/67 |
| 4,781,548 | A | | 11/1988 | Alderson et al. |

(Continued)

FOREIGN PATENT DOCUMENTS

DE   197 14 711   10/1998

(Continued)

OTHER PUBLICATIONS

Keeler, E. K., et al., "Accessory Equipment Considerations With Respect to MRI Compatibility," JMRI, 8:12-18 (1998).

(Continued)

*Primary Examiner*—Kevin Sirmons
*Assistant Examiner*—Laura C Schell
(74) *Attorney, Agent, or Firm*—Gregory L. Bradley; Henry E. Bartony, Jr.

(57) ABSTRACT

A disposable flow set for use with a pump includes a first administration tube, at least one tube-segment having a first end and a second end, the first end connected to the first administration tube, a second administration tube connected to the second end of the at least one tube-segment; and an identifying key member connected to the at least one tube-segment. The identifying key member includes a number of teeth that define a unique code, including a combination of location and width. The teeth fit into compatible niches located in the pump.

15 Claims, 4 Drawing Sheets

U.S. PATENT DOCUMENTS

| | | | |
|---|---|---|---|
| 4,854,836 A | | 8/1989 | Borsanyi |
| 4,954,812 A | | 9/1990 | Lebron |
| 4,966,579 A | | 10/1990 | Polaschegg |
| 5,018,945 A | | 5/1991 | D'Silva |
| 5,057,076 A | | 10/1991 | Polaschegg |
| 5,176,631 A | | 1/1993 | Koenig |
| 5,417,213 A | | 5/1995 | Prince |
| 5,429,602 A | | 7/1995 | Hauser |
| 5,439,451 A | | 8/1995 | Collinson et al. |
| 5,460,490 A | * | 10/1995 | Carr et al. .............. 417/44.2 |
| 5,494,036 A | | 2/1996 | Uber, III et al. |
| 5,616,124 A | | 4/1997 | Hague et al. |
| 5,681,294 A | * | 10/1997 | Osborne et al. ............ 604/251 |
| 5,739,508 A | | 4/1998 | Uber, III |
| 5,807,322 A | | 9/1998 | Lindsey et al. |
| 5,827,223 A | | 10/1998 | Butterfield |
| 5,840,058 A | * | 11/1998 | Ammann et al. ............. 604/30 |
| 5,853,397 A | | 12/1998 | Shemesh et al. |
| 5,971,972 A | * | 10/1999 | Rosenbaum ................ 604/411 |
| 6,064,797 A | | 5/2000 | Crittendon et al. |
| 6,083,206 A | | 7/2000 | Molko |
| 6,106,249 A | | 8/2000 | Barak |
| 6,106,502 A | | 8/2000 | Richmond |
| 6,203,528 B1 | | 3/2001 | Deckert et al. |
| 6,213,738 B1 | | 4/2001 | Danby et al. |
| 6,224,578 B1 | | 5/2001 | Davis et al. |
| 6,248,093 B1 | | 6/2001 | Moberg |
| 6,261,262 B1 | | 7/2001 | Briggs et al. |
| 6,475,180 B2 | * | 11/2002 | Peterson et al. .............. 604/65 |
| 2002/0127114 A1 | | 9/2002 | Barak |
| 2003/0014035 A1 | | 1/2003 | Trombley, III et al. |

FOREIGN PATENT DOCUMENTS

| | | |
|---|---|---|
| JP | HEI 7-178169 | 7/1995 |
| WO | WO 03/006101 | 1/2003 |

OTHER PUBLICATIONS

Lemieux, L., et al., "Recording of EEG During fMRI Experiments: Patient Safety," MRM, 38:943-952 (1997).

Lemieux, L., et al., "Methodological Issues in EEG-Correlated Functional MRI Experiments," International Journal of Bioelectromagnetism, vol. 1, No. 1, p. 87-95 (1999).

A Primer on Medical Device Interactions with Magnetic Resonance Imaging Systems, U. S. Food and Drug Administration, Center for Devices and Radiological Health (Feb. 7, 1997).

BodyGuard Operator's Manual, Version 06, Caesarea Medical Electronics, Ltd., Israel (May 2001).

BodyGuard Ambulatory Infusion Pump Product Brochure, Caesarea Medical Electronics, Ltd., Israel, no date.

Israeli Patent Application Serial No. 142446 filed Apr. 4, 2001, "A Flow Set and a Method to Identify Said Flow Set by a Liquid Pump," Caesarea Medical Electronics, Ltd., Israel.

Israeli Patent Application Serial No. 141137 filed Jan. 28, 2001, "Liquid Pump," Caesarea Medical Electronics, Ltd., Israel.

BodySet, IV Administration Set with Anti-siphon Valve, Male Luer Lock, CE0483, Manufactured by Teva Medical Ltd. for Caesarea Medical Electronics, Ltd., Israel (May 2001).

* cited by examiner

FLOW SET INCLUDING AN IDENTIFYING KEY MEMBER HAVING TWO PROJECTIONS COOPERATING TO DEFINE A UNIQUE CODE

BACKGROUND OF THE INVENTION

This invention relates to liquid administration and more specifically, it is concerned with a liquid flow set useful for administering liquids to a patient through a flexible tube.

Systems for administration of liquids to a patient are widely known. However, a variety of different pumps are available for propelling a liquid to a patient, which may differ, among others, by construction and safety of use.

Flow sets for use with a liquid pump must be attentively designed for safe use. A dedicated tube-segment of the tube must be installed in the pump and the tube should be installed in the right place, and tightened, straightened and stretched. The flow set should be full with liquid before using it and should remain full as long as it is in use, to prevent air injections into the patient. Moreover, the pumping tube-segment should be replaced with other tube-segments when it loses flexibility.

Further, for patient safety, the pump should be able to identify and verify that an appropriate flow set has been installed therein for use.

The present invention is concerned with a liquid flow set that includes a number of safety features, and a method for identifying the flow set by the liquid pump in which it is used.

SUMMARY OF THE INVENTION

The present invention provides a flow set for administering liquid to a patient using pumps (such as liquid pumps), a method for identifying a flow set by the pump in which it is used, and pumps for use with a flow set.

According to the teachings of the present invention, there is provided a disposable flow set for administering liquid to a patient, including at least one pumping tube-segment, connected to the first administration tube, enabling installation of the flow set in a pump, a second administration tube installed in the end of the last pumping tube-segment, and an anti-free-flow valve installed in the end of the second administration tube.

In a preferred embodiment, the flow set further includes a drip chamber or a spike, and a first administration tube to administer liquid from the drip chamber or the spike.

By a preferred embodiment, the flow set further includes at least one identifying key member, wherein each of the identifying key members is connected to each of the tube-segments. Preferably, each of the identifying key members is clamped on the tube-segment and includes a number of teeth members adapted to form a unique code or combination of location and width. The teeth are preferably adapted to be inserted into a compatible niche(s) in a specific liquid pump, thereby preventing insertion of the flow set into a non-compatible liquid pump.

In a preferred embodiment, each key member further includes a pressing-plate for pressing the tube-segment against a pressure sensor of the liquid pump. Preferably, when the door of the liquid pump is closed, it presses the pressing-plate, which, in turn, presses the tube segment against the pressure sensor, thereby enabling the liquid pump to use the sensed pressure to verify the existence of the flow set.

By another preferred embodiment of the present invention, each pumping tube-segment of the disposal flow set is bordered by a stopper at both ends thereof. The stoppers preferably are installed in fitted niches in a liquid pump.

By another preferred embodiment, the length of each pumping tube-segment of the disposal flow set is preferably in a range of 81-83 millimeters.

By another preferred embodiment, the inside diameter of each pumping tube-segments of the disposal flow set is preferably in a range between 2.5 millimeters and 2.7 millimeters, and the diameter of the first and/or second administration tube is preferably in a range between 1.1 millimeters and 1.3 millimeters.

By another preferred embodiment, the disposal flow set further includes a controller in the inlet of the drip chamber or spike, enabling control of the volume of the liquid drops entering therein.

According to another aspect of the present invention, a method is provided for identifying the flow set of the present invention. The method preferably includes (1) pre-measuring the interior volume of the flow set, (2) measuring the quantity or volume of liquid flowing into the flow set, (3) comparing the measured volume of liquid to the interior volume of the flow set, and (4) if the measured volume of the liquid used to fill the flow set is different than the interior volume of the flow set, stopping the operation of the liquid pump or activating an alarm, or both.

According to yet another aspect of the present invention, a method for conducting a priming procedure includes (1) continuously measuring the quantity of liquid flowing into the flow set and the pressure of liquid in the administration tubes, (2) pumping liquid into the flow set to empty or purge air therefrom and to fill liquid therein, (3) recognizing the first arrival of liquid to an anti-free-flow valve in the flow set, by sensing a rise of pressure in the administration tube, (4) obtaining the volume of liquid used to fill the flow set, from the measurement of liquid flow quantity until the rise of pressure is a predetermined ratio high, and (5) comparing the volume of liquid used to fill the flow set with the interior volume of the flow set.

Because the resistance of the anti-free-flow valve for air passing is significantly lower than the resistance of the anti-free-flow valve for liquid passing, the first arrival of liquid to the anti-free-flow valve can be determined. Preferably, if the volume of liquid used to fill the flow set is different than the interior volume of the flow set, the operation of the liquid pump is stopped or an alarm is activated, or both occur.

According to another aspect of the present invention, a method for identifying a flow set includes (1) pre-counting the number of entering drops, per a volume unit of liquid, which should enter the drip chamber or the spike of the flow set, (2) when operating a liquid pump, counting the drops number per supplied liquid unit, and (3) if the drops per volume unit of supplied liquid is different than the pre-counted number of drops, then stopping operation of the pump or activating an alarm, or both.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the figures.

DETAILED DESCRIPTION OF THE PREFERED EMBODIMENTS OF THE INVENTION

In one aspect, the present invention provides a flow set for administering a liquid when using a pump, and a method for identifying such a flow set by the pump in which it is used.

Flow sets for use with a liquid pump must be attentively designed for safe use. A dedicated tube-segment of the tube must be installed in the pump and the tube must be installed in the right place, and tightened, straightened and stretched. The flow set must be full with liquid before using it and should remain full as long as it in use, to prevent an air injection into a patient. Moreover, the pumping tube-segment must be replaced with other tube-segments when it loses its flexibility.

The flow set of the present invention, along with the compatible pump, has a number of features that ensures the use of only a flow set that is compatible with a liquid pump. There are stoppers in both ends that are shaped to install in fitted niches in a liquid pump. Further, the flow set includes an identifying key member that prevents the insertion of a wrong flow set into the pump, and enables liquid pressure measuring. If the pump is unable to measure the liquid pressure, the liquid pump will not start. Each tube-segment has a specific length and the system (a liquid pump with compatible flow set) uses methods of identifying the flow set that has been installed in the liquid pump.

The principles and operation of the flow set and the method for identifying the flow set, according to the present invention, may be better understood with reference to the drawings and the accompanying description.

Figure 1:
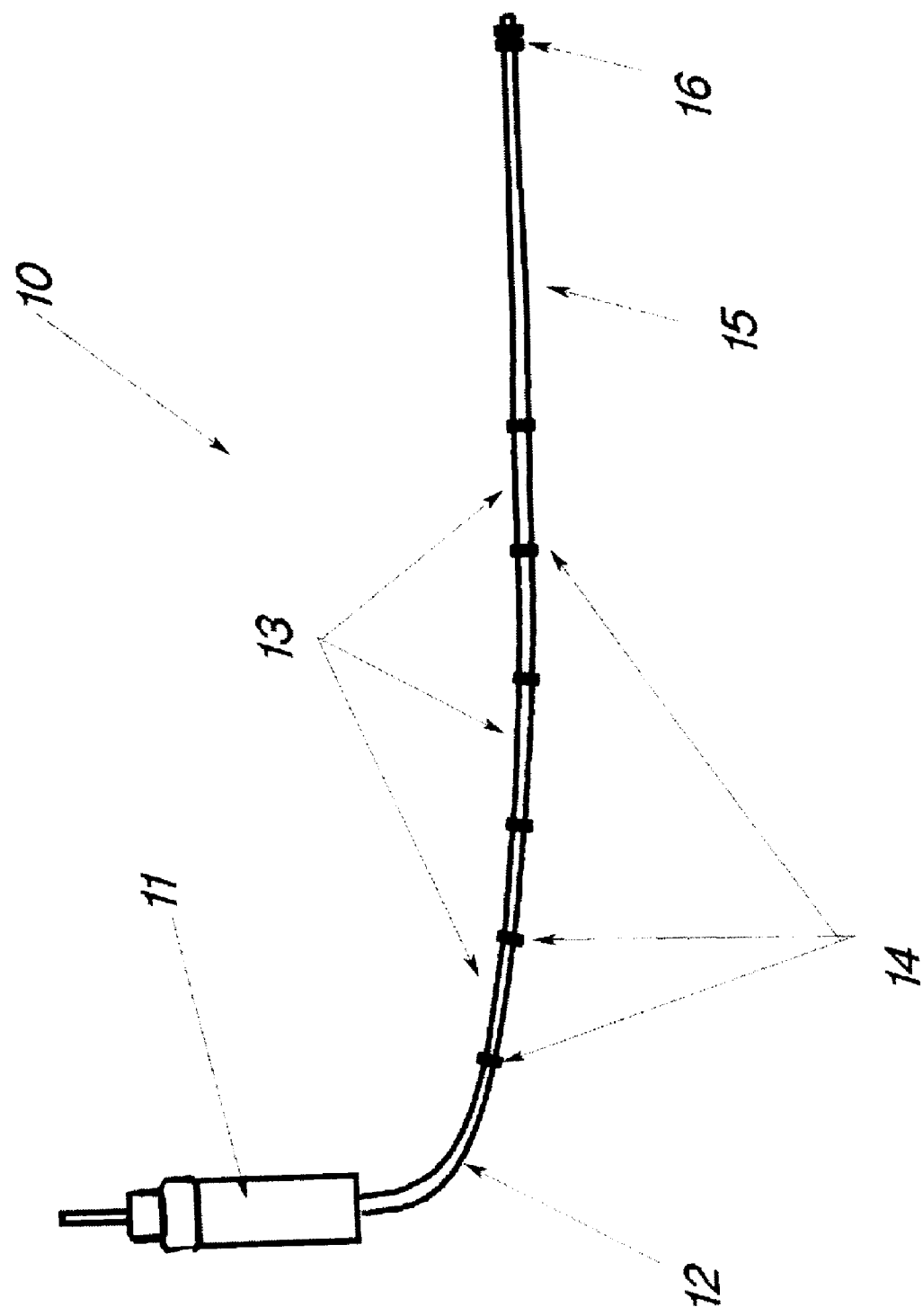
FIG. 1 illustrates a flow set with a drip chamber, a number of pumping tube-segments and an anti-free-flow valve.

Referring now to the drawings, FIG. 1 illustrates a flow set with a drip chamber, a number of pumping tube-segments and an anti-free-flow valve. A flow set 10 includes a drip chamber 11 that enables installation in a housing with drop sensors that are located in a liquid pump 17 (shown in FIG. 2). The drop sensor counts the drops passing through the drip chamber 11. A first administration tube 12 administers the liquid through the pumping tube-segments 13. Stoppers 14 border each pumping tube-segment 13 in the ends thereof. These stoppers 14 are used to install a pumping tube-segment 13 in a liquid pump in a correct position—tight, straight and stretched. A second administration tube 15 administers the pumped liquid to an anti-free-flow valve 16. An identifying key member 24 is installed on each pumping tube segment 13.

Figure 2:
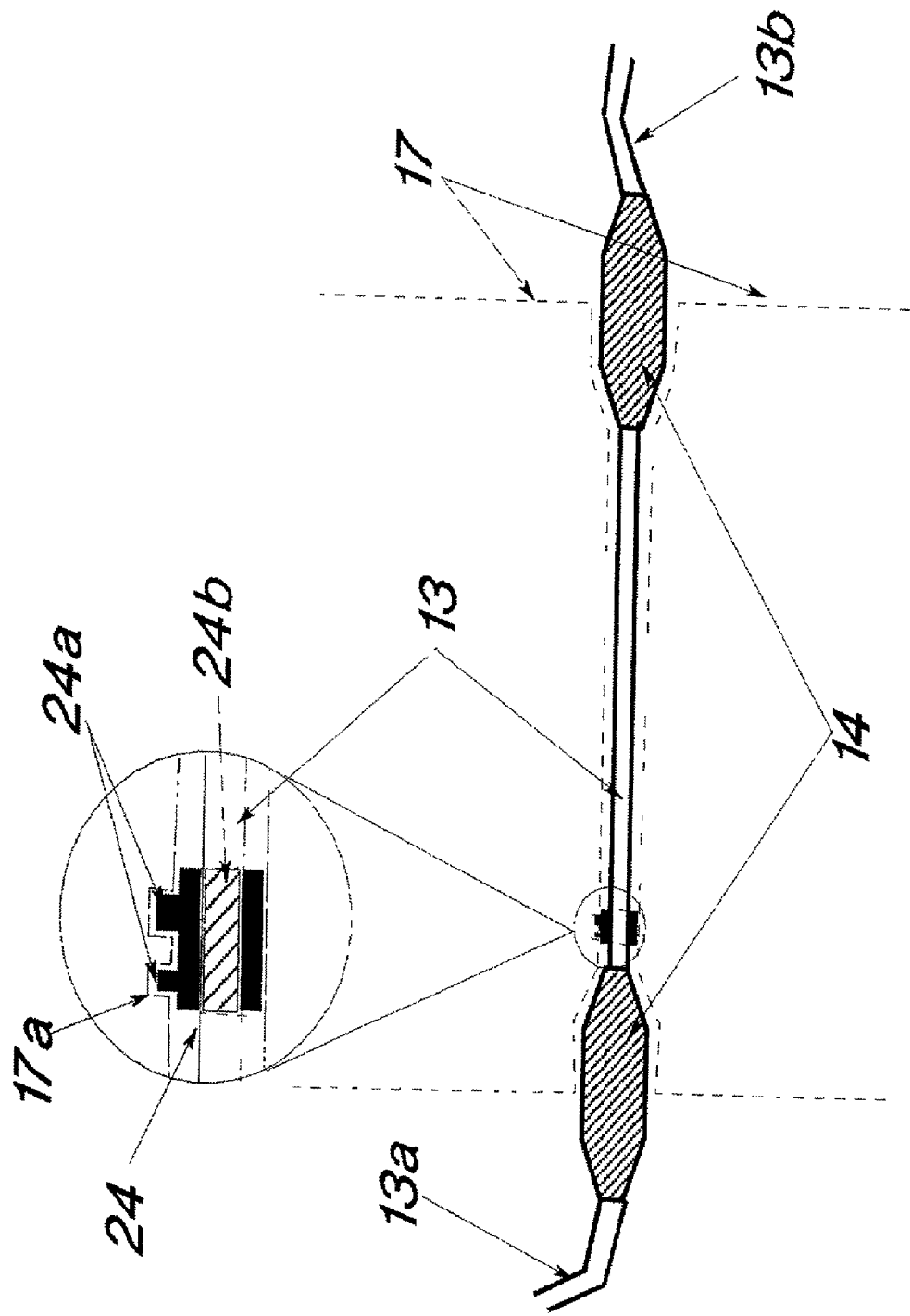
FIG. 2 illustrates a pumping tube-segment for installation in a pump.

FIG. 2 illustrates a pumping tube-segment 13 of the present invention, and a way to install the segment in a liquid pump. There are number of pumping tube-segments 13, 13a, 13b in the flow set 10. As shown, a stopper 14 at a respective end thereof borders each of the tube-segments 13.

One of the pumping tube-segments 13 is in use and installed in a liquid pump 17. An identifying key 24 is installed on the tube-segment 13. The identifying key 24 preferably surrounds or clamps the tube-segment 13 and includes a number of teeth 24a. Each tooth has a specific width and a specific location, thereby creating a code that enables insertion of the tube-segment 13 only in a liquid pump 17 that has a set of complementary niches 17a that are arranged in the same code or combination.

The identifying key 24 also includes a pressure-plate 24b. The pressure-plate 24b is pressed by the door 25 (shown in FIG. 3) of the liquid pump 17, which presses the tube-segment 13 against a pressure sensor 26 (shown in FIG. 3) that is installed in the liquid pump 17 behind the identifying key member 24. The stoppers 14 are installed in complementary niches of a liquid pump 17, and force the pumping tube-segment 13 to stay tight, straight and stretched. The identifying key 24 prevents insertion of the tube-segment 13 in a non-compatible liquid pump, and the liquid pump 17 will not start unless the pressure sensor measures pressure.

Figure 3:
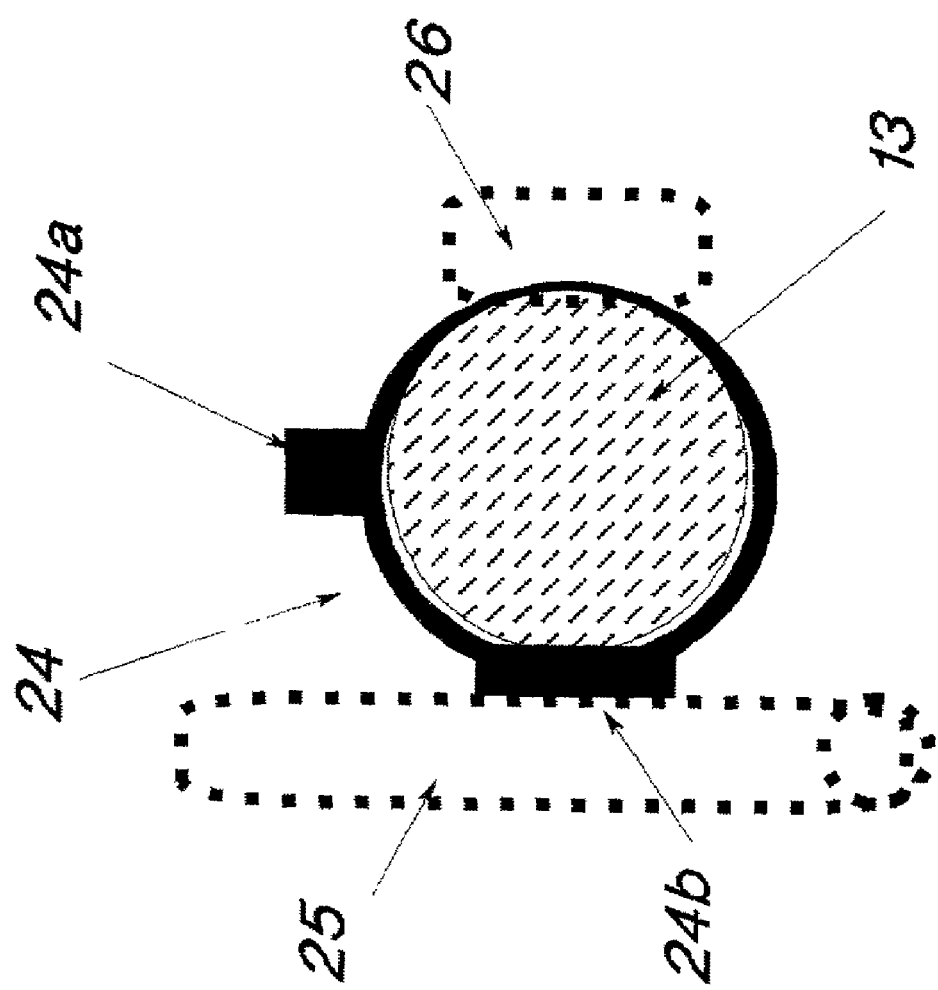
FIG. 3 illustrates a cross-section of an identifying key member.

FIG. 3 illustrates a cross-section of an identifying key 24. The identifying key 24 clamps the tube-segment 13 and includes a set of teeth 24a to enable insertion of the flow set only into a compatible liquid pump. The key 24 also includes a pressure-plate 24b, which is pressed by the door 25 of the liquid pump and, in turn, presses the tube-segment 13 against a pressure sensor 26 of the liquid pump, thereby enabling pressure measurement.

Figure 4:
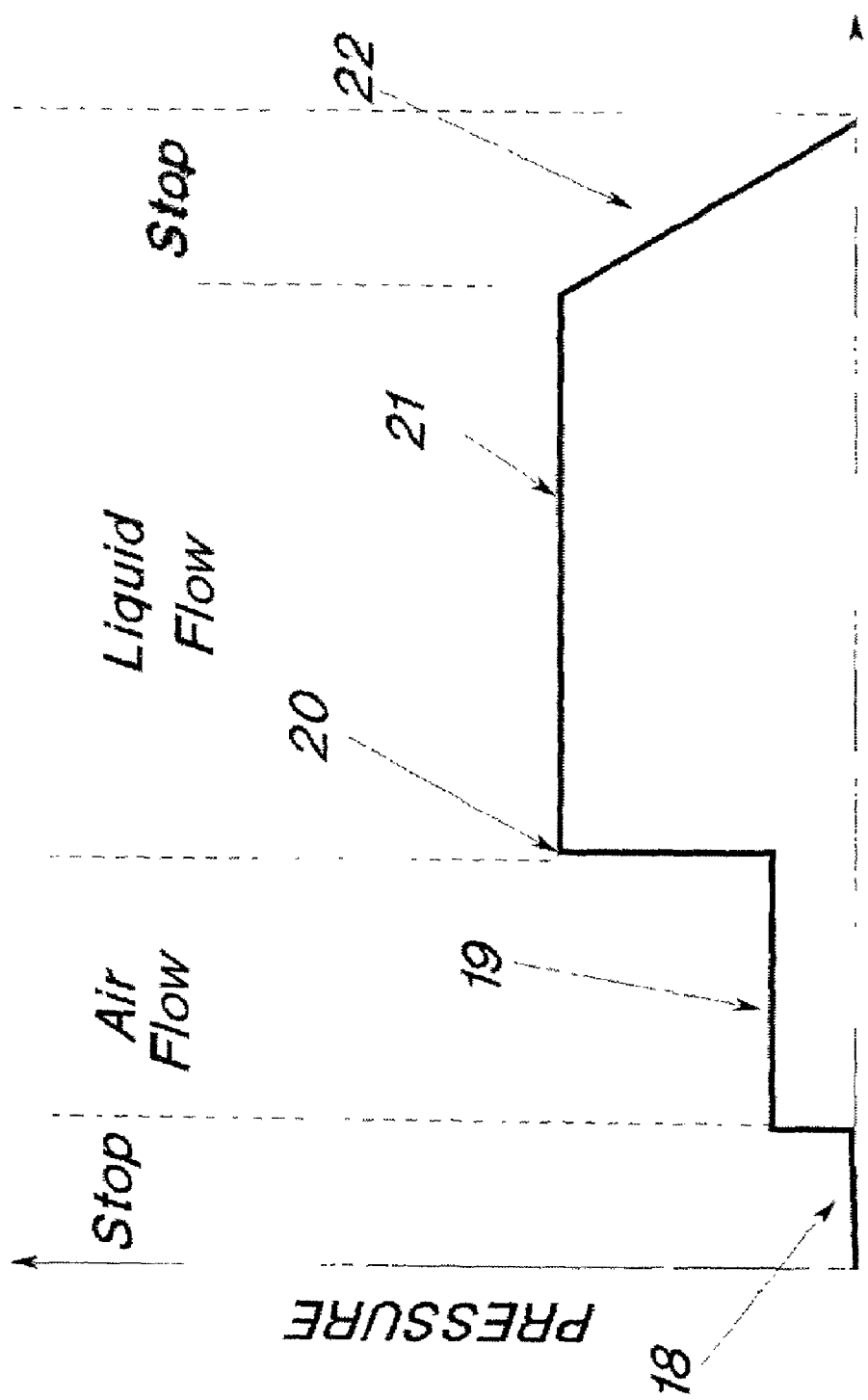
FIG. 4 illustrates a chart of the pressure inside the tube of a flow set during the priming procedure.

FIG. 4 illustrates a chart of the pressure inside the tube of a flow set during the priming procedure. When installing a flow set 10 in a liquid pump, the flow set 10 is empty and the liquid does not start to flow yet. Therefore, the pressure in the tubes is low 18. When liquid starts to flow into the administration tubes, the liquid pushes the air from the tubes out through the anti-free-flow valve 16, which has a resistance to the airflow and therefore causes the pressure to rise to a medium level 19. The liquid fills the whole flow set 10 and liquid starts to flow through the anti-free-flow valve 16. The resistance of the valve to a liquid flow is significantly higher than the resistance to airflow. Therefore, a significant rise of pressure 20 is sensed and the pressure remains high 21 as long as liquid flows through the set.

When the pump stops, the pressure slides down 22 to a low pressure. The pressure rise 20 is used by the liquid pump to determine that the flow set 10 is full. The pumps' controller compares the volume of liquid used to fill the flow set 10 with the interior volume of the flow set, and uses this information to identify the flow set. If the liquid pump does not identify the installed flow set as the required flow set, the liquid pump stops operating or an alarm is activated, or both.

In preferred embodiments, the one or more tube-segments 13 may be formed of polyvinylchloride (PVC), polyurethane or silicone.

Although the invention has been described in conjunction with specific embodiments thereof, it is evident that many alternatives, modifications and variations will be apparent to those skilled in the art. Accordingly, the present invention is intended to embrace all such alternatives, modifications and variations that fall within the spirit and broad scope of the appended claims.

What is claimed is:

1. A disposable flow set comprising:
   a first administration tube;
   at least one tube segment adapted to be placed within a liquid pump to pressurize fluid within the at least one tube-segment and having a first end and a second end, the first end connected to said first administration tube;

a second administration tube connected to the second end of the at least one tube segment; and an identifying key member connected to the at least one tube segment between the first end and the second end of the at least one tube segment, the identifying key member comprising two projections, the first projection having a first width and being located at a first position on the identifying key member and the second projection having a second width greater than the first width and being located at a second position on the identifying key member, the two projections cooperating to define a unique code comprising a combination of the first and second locations and the first and second widths of the projections.

2. The disposable flow set of claim 1, wherein the identifying key member is adapted to interact with a pressure sensor of the pump to enable measurement of pressure within the at least one tube segment.

3. The disposable flow set of claim 1, further comprising an anti-free-flow valve installed in the end of said second administration tube.

4. The disposable flow set of claim 1 wherein the two projections cooperate with corresponding niches in the liquid pump.

5. The disposable flow set of claim 4 wherein the two projections are adapted to be inserted into compatible niches in the pump.

6. The disposable flow set of claim 1 wherein the identifying key member comprises a pressing-plate for pressing the at least one tube segment against a pressure sensor of the pump, the pump adapted to use the sensed pressure to verify the existence of the flow set.

7. The disposable flow set of claim 6 wherein a door of the pump is adapted to press the pressing-plate.

8. The disposable flow set of claim 1 wherein the at least one tube segment is bordered by a stopper in both ends, the stoppers being configured to install in fitted niches in a pump and maintain the tube-segment in a straightened state.

9. The disposable flow set of claim 1 wherein the length of the at least one tube segment is between 81 millimeters and 83 millimeters.

10. The disposable flow set of claim 1 wherein the inside diameter of the at least one tube segment is between 2.5 millimeters and 2.7 millimeters.

11. The disposable flow set of claim 1 wherein the diameter of said first and second administration tubes is between 1.1 millimeters and 1.3 millimeters.

12. The disposable flow set of claim 1 wherein the at least one tube segment comprises a plurality of identifying key members, each identifying key member comprising a number of projections.

13. The disposable flow set of claim 1 wherein the two projections extend outward beyond a circumference of the at least one tube segment.

14. The disposable flow set of claim 1 wherein the identifying key member is connected to the at least one tube segment between the first end and the second end of the at least one tube segment around the circumference of the tube segment.

15. The disposable flow set of claim 1 wherein the identifying key member comprises a housing connected around the circumference of the at least one tube segment between the first end and the second end of the at least one tube segment, the two projections extending outward from the housing.

* * * * *